United States Patent [19]

Metzner

[11] Patent Number: 5,142,002
[45] Date of Patent: Aug. 25, 1992

[54] COMPOSITIONS FOR GERM REMOVAL FROM WATER

[75] Inventor: Peter Metzner, München-Martinsried, Fed. Rep. of Germany

[73] Assignee: Bayrol Chemische Fabrik GmbH, Fed. Rep. of Germany

[21] Appl. No.: 442,117

[22] Filed: Nov. 28, 1989

[30] Foreign Application Priority Data

Nov. 28, 1988 [DE] Fed. Rep. of Germany ....... 3840103

[51] Int. Cl.$^5$ .................. C08F 283/00; C08G 61/00; C08G 73/00; A61K 31/14
[52] U.S. Cl. .................................... 525/540; 528/397; 528/422; 252/175; 514/642; 424/78.09
[58] Field of Search ............... 424/79, 78, 78.09; 564/503; 514/642; 525/540; 528/397, 422; 252/175

[56] References Cited

U.S. PATENT DOCUMENTS

3,898,336 8/1975 Rembaum et al. .................. 424/25
4,098,602 7/1978 Seymour et al. ..................... 71/67

FOREIGN PATENT DOCUMENTS

| 0059978 | 3/1982 | European Pat. Off. . |
| 0203892 | 5/1986 | European Pat. Off. . |
| 2235539 | 2/1974 | Fed. Rep. of Germany . |
| 2438035 | 2/1975 | Fed. Rep. of Germany . |
| 2530487 | 1/1977 | Fed. Rep. of Germany . |
| 2600466 | 2/1977 | Fed. Rep. of Germany . |
| 2911288 | 10/1980 | Fed. Rep. of Germany . |
| 3247536 | 3/1984 | Fed. Rep. of Germany . |
| 3423703 | 1/1986 | Fed. Rep. of Germany . |
| 2194227 | 3/1988 | United Kingdom . |
| 8702221 | 4/1987 | World Int. Prop. O. . |

OTHER PUBLICATIONS

Beck et al., "Recommendations for the Testing and the Evaluation of the Efficacy of Chemical Disinfectant Procedures", Zbl. Bakt. Hyg., 1. Abt. Orig. B 165, 335–380 (1977).

Houben-Weyl, Methoden der organischen Chemie, Georg Thieme Verlag, Stuttgart and New York, 1987, vol. E20, chapter 2,3 "Poly/ionene".

*Primary Examiner*—Frederick E. Waddell
*Assistant Examiner*—Diane Gardner
*Attorney, Agent, or Firm*—Brumbaugh, Graves, Donohue & Raymond

[57] ABSTRACT

In a process for the elimination of germs, especially the removal of algae from water by means of water soluble quaternary ammonium compositions a polymeric salt of formula (I)

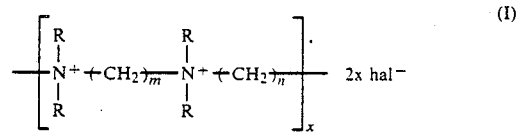

wherein
R is a $C_1$-$C_7$ hydrocarbon group,
m and n are a number of from 4 to 12 regardless of each other,
x is a number of from 10 to 300, and
hal is chlorine, bromine, or iodine is added to the water as the quaternary ammonium composition in an amount of more than 0.1 ppm and the process is carried out in the absence of heavy metal ions.

5 Claims, No Drawings

COMPOSITIONS FOR GERM REMOVAL FROM WATER

FIELD OF THE INVENTION

The invention relates to a process for the elimination of germs, especially the removal of algae from water by using water soluble quaternary ammonium compositions as well as to a compound which can be used as an algicide and/or bactericide in water systems.

BACKGROUND OF THE INVENTION

Chlorine in the form of chlorine gas or sodium hypochlorite has been used for a long time and in great amounts to remove algae from water and also for the oxidative decomposition of oxidizable impurities contained in water. This chlorination, however, has a number of disadvantages in the purification of water and water systems, such as a pungent odor and the tendency to irritate the mucous membranes. Furthermore, it was found that the chlorination of water may lead to the formation of halide compositions which must be regarded as being carcinogenic. The same is true if bromine is used instead of chlorine.

For this reason many attempts were made to use halide-free disinfectants instead of the halide compositions in the treatment of water, especially water in swimming pools. The use of peroxide compositions, for example hydrogen peroxide, sodium or potassium persulfate for degerming water has been known for a long time. It is likewise known to attack the growth of algae by means of copper ions and to make water germ free by means of silver salts. Descriptions are found also of a combination of peroxide compositions and silver or copper ions as well as the combination of quaternary ammonium compositions and hydrogen peroxide (c.f. DE-A-2 235 539, DE-A-2 530 487 and DE-A-2 911 288).

DE-A-2 600 466 and DE-A-3 423 703 describe methods of preventing the growth of algae in aqueous systems wherein the algae are contacted with a condensation product of tetramethylethylenediaminedihydrochloride and epichlorohydrine. DE-A-3 247 536 discloses algicide condensates of diamino alkanes and urea or epichlorohydrine. However, it was found that these condensates are not satisfactory in their algicide effect so that usually they are applied in combination with heavy metal ions in order to achieve sufficient effectiveness.

Algicide mixtures based on monomer quaternary ammonium compositions and copper salts are disclosed in U.S. Pat. No. 4,098,602. The ammonium compositions used in that case are salts of the benzalkonium type. These compositions, however, lead to the undesired formation of foam and have the further disadvantage of developing a disturbing odor.

EP-A-59 978 describes a process for the removal of algae wherein a quaternary ammonium composition is used in combination with water soluble copper salts and/or silver salts and a peroxide composition setting free oxygen. Suitable quaternary ammonium compositions are poly(diallyldimethylammoniumchloride), poly(1,4-bis(dimethylazonia)-7-oxanonylenedichloride) and poly(1,4-bis(dimethylazonia)-6-hydroxyheptylenedichloride).

The use of a condensation product of tetramethylhexamethylenediamine and 1,3-di-bromopropane is described as a bactericide, especially in combination with copper and silver ions, in WO 87/02221. An algicide effect of this condensate is not mentioned.

GB-A-2 194 227 discloses the use of a polymeric cationic quaternary ammonium composition together with a copper salt, a gelating agent, and an oxidizing agent for the treatment of water, especially in swimming pools.

Yet it was found that the quaternary ammonium compositions of the benzalkonium type used to remove algae from water tend to form foam and, what is more, have an unpleasant odor. The polymeric quaternary ammonium compositions, on the other hand, have an insufficient algicide effect and, therefore, as a rule, must be used in combination with metal ions, such as copper, silver, or manganese ions. The addition of such metal ions, however, is undesired for various reasons. For instance, the addition of copper and silver ions leads to increased corrosion of the metal tubes present in the water system under treatment because of the series of electrochemical potentials. Under the influence of reducing agents and with the effect of light silver ions provide black silver deposits. Furthermore, the use of heavy metal ions is undesirable for reasons of price and for reasons of environmental protection.

EP-A-0 203 892 finally describes the use of polymeric ammonium compositions to fight noxious organisms in water systems, the dimethylammonium groups of these compositions being separated alternatingly by alkylene groups and dibenzyl groups. DE-A-24 38 035 describes biocide mixtures which consist of chemical complexes or mixtures of a quaternary ammonium composition and an isothiazolin-3-on-composition.

SUMMARY OF THE INVENTION

It is an object of the present invention to provide a process for the elimination of germs, especially the removal of algae, from water wherein the disadvantages described above are avoided. To accomplish that, it is necessary to find a composition which has the desired algicide effectiveness and yet does not tend to form foam and which displays its maximum effectiveness even without the addition of heavy metal ions.

That object is met by the process of the kind defined initially and characterized by the fact that a polymeric salt of formula (I)

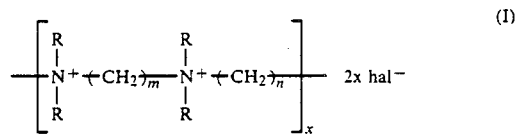

wherein
R is a $C_1-C_7$ hydrocarbon group,
m and n are a number from about 4 to 12 independently of each other,
x is a number from about 10 to 300, and
hal is chlorine, bromine, or iodine
is added to the water as the quaternary ammonium composition in an amount of more than 0.1 ppm.

The subject matter of the invention also involves a compound for degerming, particularly for removing algae from water, for which compound contains a water soluble polymeric quaternary ammonium composition of formula (I).

In the polymeric ammonium compositions of formula (I) R is a hydrocarbon radical including from 1 to 7 carbon atoms. Preferably R is methyl, ethyl, or benzyl, with methyl being especially preferred.

The indices m and n characterize the chain length of the alkylene groups between the nitrogen atoms represent a number from about 4 to 12, independently of each other. This means that each individual one of the alkylene groups of the polymeric chain comprises from about 4 to 12 carbon atoms, while the individual alkylene units may differ from each other as to their number of carbon atoms. Within the polymer chains m and n each may have different values, depending on the starting materials used, i.e. m may have 2 or 3 different values within a polymer chain, the same being true of n. As a rule, however, m and n within one polymer chain each have unvarying values. In this event the respective alkylene units occur alternatingly.

Especially prefered are those polymer ammonium compositions in which either one of m and n is 6 and the respective other one a number from about 4 to 12. Again, the particularly preferred quaternary ammonium compositions are those in which one of m and n is 6 and the other one is 4, 6, or 12. Very particularly preferred are compositions in which both m and n are 6. In this manner polymers are obtained in which the respective ammonium groups are separated by alkylene groups of the same length.

It is possible as well to provide the polymer chains with varying proportions of alkylene groups of different lengths. For example, one of m and n may be 6, while the respective other one is 4, 6, or 12, and these being present in different proportions. It is possible, for example, to produce polymers which contain 80% of hexamethylene units and 10% each of tetramethylene and dodecamethylene groups. Depending on the starting material used, these different alkylene groups may be distributed statistically or in a more or less orderly fashion throughout the polymer chain.

Polymeric ammonium compositions of formula (I) wherein m or n is smaller than 4 do not have the desired strong algicide effect. For example, a polymer ammonium composition in which m=5 and n=2 has greatly reduced effectiveness and a composition in which m and n are 2 is even less effective. Optimum results are obtained with polymeric ammonium compositions of formula (I) in which at least one of m and n is 6.

The chain length of the polymers of formula (I) used according to the invention may vary within wide limits. For example polymeric ammonium compositions of a molecular weight of up to 40000 may be used, depending on the kind of production. In general, x is a number of from about 10 to 300, preferably from 50 to 200. Most preferred are ionomers in which x is 100 to 150.

The process according to the invention permits the use of quaternary ammonium compositions of formula (I) together with an oxidizing agent. Suitable oxidizing agents, for example, are compositions which set free oxygen, such as sodium and potassium persulfate and peroxidisulfate, as well as aqueous solutions of hydrogen peroxide. Other peroxide compositions may be used as well. Other suitable oxidizing agents, for example, are trichlorisocyanuric acid, sodium chlorisocyanurate and hypochlorous acid. Especially preferred are potassium and sodium monopersulfate and peroxidisulfate, $Na_2SO_5$ and $K_2SO_5$ or $Na_2S_2O_8$ and $K_2S_2O_8$ as they display excellent efficiency when used together with the quaternary ammonium compositions of formula (I) and no elemental chlorine is formed when they are applied.

The polymeric ammonium compositions of formula (I) may be used together with other customary additives, such as conditioners, stabilizers, dissolving intermediaries, dissolving adjuvants, etc. The presence of such additives may be necessary particularly for the production, storage, and stabilizing as well as for the use of the mixtures according to the invention.

When applying the process according to the invention, the quaternary ammonium compositions of formula (I) preferably are used in quantities from about 0.1 to 10 ppm, based on the water to be treated. Preferred quantities are 0.2 to 5 ppm. Usually only one polymeric ammonium composition of formula (I) is used. But it is possible also for several of these compositions to be given at the same time. Apart from the polymers of formula (I), other compositions of algicide and/or bactericidal effect may be used, particularly so if their presence is advantageous to achieve special effects, such as in fighting special types of algae or bacteria.

The process according to the invention is based on the finding that the polymer ammonium compositions of formula (I) dispose of excellent and broad algicide effectiveness which is much more pronounced than that of other (polymer) quaternary ammonium compositions. The quality of the algicide effect essentially depends on the chain length of the alkylene groups located between the individual ammonium groups. If there are less than 4 or more than 12 methylene groups, the algicide effect is insufficient; the optimum is achieved at a chain length of 6 methylene groups. High algicide effect is achieved also if different chain lengths which, however, lie within the ranges indicated, are used within one polymer chain. Once considerable amounts of alkylene groups having less than 4 or more than 12 carbon atoms are given, however, the algicide effect is clearly reduced.

The polymeric ammonium compositions used in accordance with the invention not only have an algicide effect but also considerably bacteriostatic and/or bactericide efficiency. This is advantageous especially if the process according to the invention is applied to the removal of algae from swimming pools. Here it is important to keep the concentrations of bacteria within tolerable limits, whereas no complete sterility is necessary.

A number of advantages are obtained from the use of the polymeric ammonium compositions according to the invention. For example, the use of elemental chlorine or of compositions which set free elemental chlorine may be dispensed with since such a combination is quite possible. Furthermore, the use of heavy metal ions, such as copper, silver, and manganese ions may be dispensed with. Such use is becoming ever more problematic and is undesirable, among others, for reasons of the protection of the environment and waters. Finally, in addition to the algicide effect desired in the first place, quite a considerable bacteriostatic or even bactericide effect is obtained.

The process in accordance with the invention and suitable polymeric ammonium compositions for the same or of compounds containing the same are suitable in the first place for the removal of algae from swimming pools. Yet they maybe applied in other water systems as well as where the absence of algae is important, such as in cooling towers and cooling systems as well as in water reservoirs for technical or industrial purposes.

The making of the compositions to be used in accordance with the invention is known as such. Reference is made in this context to Houben-Weyl, Methoden der organischen Chemie, Georg Thieme Verlag, Stuttgart und New York, 1987, vol. E20, chapter 2.3 "Poly/ionene)", p. 1491 et seqq. and the literature cited. Further manufacturing methods are known from U.S. Pat. No. 3,898,336.

The production usually starts from a diamine of formula (II)

$$R_2N{+}CH_2{\overline{)_m}}NR_2 \quad (II)$$

which is reacted with a dihalide composition of formula (III)

$$hal{+}CH_2{\overline{)_n}}hal \quad (III)$$

forming the polymer ionene (I)

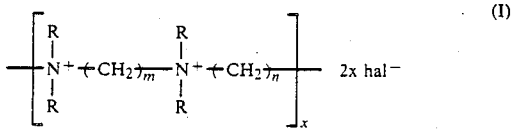

wherein the abbreviations are as defined above.

It is likewise possible to react several compositions of formula (II) in which R and/or m each are defined differently, while complying with the above definitions, with one or more compositions of formula (III). In this case the products obtained are polymer ionenes in which different substituents R and/or alkylene groups of different chain lengths and/or mixtures of halogen ions are contained.

To prevent the polymeric ammonium compositions obtained from having covalently bound halogen atoms in the end positions, preferably the reaction is carried out with the diamine of formula (II) at a minor excess over the dihalide composition. In this manner polymeric ammonium compositions are obtained in which the polymeric chains are limited in the end positions by groups of formula (IV)

The compounds according to the invention containing the algicide polymeric ammonium compositions of formula (I) in general consist from about 50 to 100% by weight of quaternary ammonium compositions of formula (I), from 0 to 95% by weight of a strong oxidizing agent, and from 0 to 50% by weight of customary additives and adjuvants. These mixtures are added to the water to be treated in quantities which guarantee a concentration of more than 0.1 ppm, based on the weight of the polymeric ammonium composition of formula (I). The mixtures may be added as a liquid concentrate in a aqueous, diluted solution or in the form of powder or tablets.

The production of the polyammonium compositions of formula (I) for use in accordance with the invention will be explained with reference to the examples below.

EXAMPLE 1

Poly [(dimethylammoniono)-1,6-hexylenebromide]

(R=CH₃; m=n=6)

A mixture of 6.883 g (40 mmol) 1,6-bis-dimethylaminohexane and 9.758 g (40 mmol) 1,6-dibromohexane is filled up with dimethylformamide/methanol (1:1) to a total volume of 27 ml and kept at 20° C. for 2 days. The colorless solid is separated, dissolved in 10 ml of water, precipitated by dripping of the solution into 200 ml of acetone and dried under vacuum at 50° C.; yield: 8.7 g (71%) (colorless powder); n=26.8 ml/g (4M potassium bromide solution); mol mass: approx. 35000.

EXAMPLE 2

Poly [1,5-bis(dimethylazonia)nonylenedibromide]

(R=CH₃; m=3; n=4

6.26 g of N,N,N',N'-tetramethyl-1,3-diaminopropane and 10.4 g of 1,4-dibromobutane were dissolved in 25 ml of methanol. The resulting solution was equilibrated for a week at 25° C. The subsequent analysis showed a reaction of 99.5% of the material used originally. The solvent then was withdrawn under vacuum and the resulting polymer was dried under vacuum for 24 hours at 40° C., yielding 16.7 g of the polymeric product; yield: 88%; n=19.4 ml/g (0.5M KBr).

Comparative tests were made to demonstrate the surprising effectiveness of the polymeric ammonium compositions to be used according to the invention. The results thereof are contained in the tables below. The test algae used were of the species Chlorella and a globular green alga. Furthermore, the bactericidal speed was measured on various test germs. The measurement was done in compliance with the recommendations "Empfehlungen für die Prüfung und Bewertung der Wirksamkeit chemischer Desinfektionsverfahren", Zbl. Bakt. Hyg. I, Abt. Orig. B 165, 335 to 380 (1977). The test germs used were *Escherichia coli, Pseudomonas aeruginosa* and *Staphylococcus aureus*. The results of the tests are listed in tables 1 to 7.

The algicide effectiveness was judged both visually (vis.) and photometrically (phot). The following abbreviations are used in the tables:

| visual assessment: | |
|---|---|
| ++++ | very strong growth |
| +++ | strong growth |
| ++ | growth |
| + | limited growth |
| − | no growth |
| Q 6/6 | polyions with R = CH₃, m = 6, n = 6, hal = Cl |
| Q 4/6 | polyions with R = CH₃, m = 4, n = 6, hal = Cl |
| Q 12/6 | polyions with R = CH₃, m = 12, n = 6, hal = Cl |
| Q-mix | polyions with R = CH₃, hal = Cl, 80% C₆-, 10% C₄- and 10% C₁₂-alkylene |
| DDBA | dodecyldimethylbenzylammoniumchloride |
| polymer W | poly(1,4-bis(dimethylazonia)-6-hydroxyheptylene dichloride) |
| polymer H | poly(diallyldimethylammoniumchloride) |

Table 1 shows the effectiveness of various polymer ammonium compositions as against a test organism of the species Chlorella, after an incubation time of 11 days and 14 days, respectively, as compared to a conventional algicide.

All compositions were added in 50% aqueous solution until the concentrations were achieved that are listed in table 1.

Among the polymer compounds tested Q 6/6 showed full algicide effectiveness at a concentration of no more than 0.5 ppm, and this is comparable with dodecylmethylbenzylammoniumchloride which is known to be a highly effective algicide.

Table 2 shows the effectiveness of the polymeric ammonium composition Q 6/6 when used against an alga of the species Chlorella upon 2 weeks of incubation time. Known algicides (polymer W; DDBA) were tested at the same time for purposes of comparison. The algicide effect of Q 6/6 is much better than that of polymer W which has been used for a long time as an algicide in water treatment.

It was shown that the algicide effect of Q 6/6 begins at approximately 0.5 ppm. The content of copper ions has no influence worth mentioning on the algicide effectiveness against this alga. Table 3 shows that copper ions have no influence upon the effectiveness of Q 6/6.

Table 4 illustrates the effectiveness of a number of algicide compositions on a globular green alga after an incubation time of 14 days. The results of table 3 were achieved by a composition which contained 30% of active ingredient.

The polymeric ammonium compositions of formula (I) proved to be superior over other known compounds (polymer H, polymer W) or at least equivalent to the same (DDBA). In contrast to DDBA, however, Q 6/6 or Q-mix are foamless and odorless compounds.

The polymeric ammonium compositions of formula (I) further have considerable bactericidal effect on various microorganisms, as may be gathered from tables 5 to 7.

The polymeric ammonium composition Q 6/6 has bactericidal effect in combination with potassium monopersulfate in the presence or absence of copper-II-ions. This effectiveness is a little less against *E. coli* than that of a comparative preparation on the basis of the known compound polymer W. On the other hand, it is clearly better against *P. aeruginosa*. In this case polymer W is practically ineffective. The effectiveness against *S. aureus* is comparable to that of the polymer W.

It is remarkable that the *P. aeruginosa* which is relevant for the treatment and disinfection of swimming pool water and which is mentioned as a germ to be tested in DIN 19643 is reduced by almost four powers of ten by the combination of Q 6/6+Bayroklar (R) within no more than 5 minutes.

TABLE 1

Algicide effect on Chlorella sp., depending upon concentration, after incubation times of 11 and 14 days, respectively

| conc. ppm | Q 6/6* (vis) | Q 6/6* (phot) | Q 4/6* (vis) | Q 4/6* (phot) | Q 12/6* (vis) | Q 12/6* (phot) | Q 4/4** (vis) | Q 4/4** (phot) |
|---|---|---|---|---|---|---|---|---|
| 0.0 | ++++ | 0.28 | ++++ | 0.28 | ++++ | 0.28 | ++++ | 0.24 |
| 0.5 | − | 0.04 | ++ | 0.14 | ++ | 0.12 | ++ | 0.10 |
| 1.0 | − | 0.03 | ± | 0.05 | − | 0.05 | − | 0.04 |
| 1.5 | − | 0.03 | − | 0.03 | − | 0.03 | − | 0.03 |
| 2.0 | − | 0.03 | − | 0.03 | − | 0.03 | − | 0.03 |
| 2.5 | | | − | 0.03 | − | 0.03 | − | 0.02 |
| 3.0 | | | | | | | − | 0.03 |

*incubation time 11 days
**incubation time 14 days

TABLE 2

Algicide effect on Chlorella, depending upon concentration, after incubation time of 14 days

| conc. ppm | Q 6/6 (vis) | Q 6/6 (phot) | DDBA (vis) | DDBA (phot) | polymer W (vis) | polymer W (phot) |
|---|---|---|---|---|---|---|
| 0.0 | ++++ | 0.24 | ++++ | 0.24 | ++++ | 0.24 |
| 0.5 | − | 0.04 | ++ | 0.10 | ++++ | 0.23 |
| 1.0 | − | 0.03 | − | 0.04 | ++ | 0.17 |
| 2.0 | − | 0.03 | − | 0.03 | ++ | 0.11 |
| 3.0 | − | 0.03 | − | 0.03 | ++ | 0.10 |
| 4.0 | − | 0.03 | − | 0.03 | + | 0.07 |
| 5.0 | − | 0.03 | − | 0.03 | − | 0.04 |

TABLE 3

Algicide effect on Chlorella, depending upon concentration, after incubation time of 14 days

| conc. ppm | Q 6/6 (vis) | Q 6/6 (phot) | Q 6/6 + $Cu^{++}$ * (vis) | Q 6/6 + $Cu^{++}$ * (phot) | Q 6/6 + $Cu^{++}$ ** (vis) | Q 6/6 + $Cu^{++}$ ** (phot) |
|---|---|---|---|---|---|---|
| 0.0 | ++++ | 0.24 | ++++ | 0.24 | ++++ | 0.24 |
| 0.5 | − | 0.04 | − | 0.03 | − | 0.03 |
| 1.0 | − | 0.03 | − | 0.03 | − | 0.03 |

*10 parts by weight of $Cu^{2+}$ per 100 parts by weight of Q 6/6
*5 parts by weight of $Cu^{2+}$ per 100 parts by weight of Q 6/6

TABLE 4

Algicide effect on a globular green alga, depending upon concentration, after incubation time of 14 days

| conc./ppm | polymer H (vis) | polymer H (phot) | Q-Mix (vis) | Q-Mix (phot) | polymer W (vis) | polymer W (phot) | Q 6/6 (vis) | Q 6/6 (phot) | DDBA (vis) | DDBA (phot) |
|---|---|---|---|---|---|---|---|---|---|---|
| 0 | +++ | 0.22 | +++ | 0.22 | +++ | 0.22 | +++ | 0.22 | +++ | 0.22 |
| 0.3 | +++ | 0.21 | +++ | 0.20 | +++ | 0.17 | +++ | 0.19 | +++ | 0.15 |
| 0.6 | +++ | 0.20 | +++ | 0.19 | +++ | 0.18 | +++ | 0.18 | +++ | 0.14 |
| 0.9 | +++ | 0.20 | +++ | 0.19 | +++ | 0.18 | +++ | 0.15 | +++ | 0.12 |
| 1.2 | +++ | 0.20 | +++ | 0.18 | +++ | 0.17 | ++ | 0.12 | ++ | 0.12 |
| 1.8 | +++ | 0.19 | +++ | 0.16 | +++ | 0.18 | + | 0.12 | + | 0.11 |
| 2.4 | +++ | 0.19 | ++ | 0.16 | ++ | 0.16 | − | 0.10 | + | 0.10 |
| 3.0 | +++ | 0.19 | + | 0.14 | ++ | 0.15 | − | 0.08 | − | 0.10 |
| 3.6 | +++ | 0.18 | − | 0.10 | ++ | 0.14 | − | 0.08 | − | 0.08 |
| 4.2 | +++ | 0.18 | − | 0.08 | ++ | 0.14 | − | 0.09 | − | 0.08 |
| 4.8 | ++ | 0.18 | − | 0.09 | ++ | 0.13 | − | 0.08 | − | 0.08 |

TABLE 5

Bactericide effect on E. coli in tap water; germ density 2.7 × 10⁶ KBE/ml (residual germ density in KBE/ml; log RF)

| | | 0.5 min. | 1 min. | 3 min. | 5 min. | 15 min. |
|---|---|---|---|---|---|---|
| (A) | 7.5 ppm Q 6/6 0.5 ppm $Cu^{2+}$ 10.0 ppm Bayroklar(R) | $3 \times 10^4$ (1.95) | $6 \times 10^3$ (2.65) | 400 (3.83) | 70 (4.59) | 10 (5.4) |
| (B) | 7.5 ppm Q 6/6 10.0 ppm Bayroklar(R) | $2.7 \times 10^5$ (1.0) | $1.5 \times 10^5$ (1.26) | $8 \times 10^3$ (2.53) | 650 (3.62) | 60 (4.65) |
| (C) | 7.5 ppm polymer W 0.5 ppm $Cu^{2+}$ 10.0 ppm Bayroklar(R) | $1.5 \times 10^4$ (2.26) | $2 \times 10^3$ (3.13) | 170 (4.2) | 20 (5.13) | 10 (5.4) |
| (D) | 7.5 ppm polymer W 10.0 ppm Bayroklar(R) | $1.4 \times 10^5$ (1.29) | $1 \times 10^5$ (1.43) | $3 \times 10^3$ (2.95) | 180 (4.18) | 30 (4.95) |

TABLE 6

Batericide effect on P. aeruginosa; germ density 1 × 10⁶ KBE/ml tap water (residual germ density in KBE/ml; log RF)

| | | 0.5 min. | 1 min. | 3 min. | 5 min. | 15 min. |
|---|---|---|---|---|---|---|
| (E) | 7.5 ppm Q 6/6 0.5 ppm $Cu^{2+}$ 10.0 ppm Bayroklar(R) | $6 \times 10^4$ (1.22) | $3.4 \times 10^3$ (2.47) | 130 (3.89) | 40 (4.4) | 10 (5) |
| (F) | 7.5 ppm Q 6/6 10.0 ppm Bayroklar(R) | $3.8 \times 10^5$ (0.42) | $1.2 \times 10^4$ (1.92) | $7.4 \times 10^2$ (3.13) | 200 (3.7) | 10 (5) |
| (G) | 7.5 ppm polymer W 0.5 ppm $Cu^{2+}$ 10.0 ppm Bayroklar(R) | $4.1 \times 10^5$ (0.39) | $2 \times 10^4$ (1.7) | 810 (3.1) | 300 (3.52) | 110 (3.96) |
| (H) | 7.5 ppm polymer W 10.0 ppm Bayroklar(R) | $1 \times 10^6$ (0) | $1 \times 10^6$ (0) | $7.1 \times 10^5$ (0.15) | $7.0 \times 10^5$ (0.15) | $3 \times 10^5$ (0.52) |

TABLE 7

Bactericide effect on S. aureus; germ density 9.5 × 10⁵ KBE/ml tap water (residual germ density in KBE/ml; log RF)

| | | 0.5 min. | 1 min. | 3 min. | 5 min. | 15 min. |
|---|---|---|---|---|---|---|
| (I) | 7.5 ppm Q 6/6 0.5 ppm $Cu^{2+}$ 10.0 ppm Bayroklar(R) | $1.2 \times 10^4$ (1.9) | 900 (3.0) | 50 (4.28) | 20 (4.68) | 10 (4.68) |
| (J) | 7.5 ppm Q 6/6 10.0 ppm Bayroklar(R) | $4.5 \times 10^5$ (0.32) | $1.2 \times 10^5$ (0.99) | $5.6 \times 10^3$ (2.23) | $3.5 \times 10^2$ (3.43) | 20 (4.48) |
| (K) | 7.5 ppm polymer W 0.5 ppm $Cu^{2+}$ 10.0 ppm Bayroklar(R) | $3.6 \times 10^4$ (0.42) | $3.3 \times 10^3$ (2.46) | $1.2 \times 10^2$ (3.99) | 90 (4.02) | 10 (4.98) |
| (L) | 7.5 ppm polymer W 10.0 ppm Bayroklar(R) | $3.6 \times 10^5$ (0.18) | $5.6 \times 10^5$ (0.23) | $4.1 \times 10^4$ (1.36) | $1.3 \times 10^3$ (2.86) | 30 (4.5) |

What is claimed is:

1. A composition for degerming water substantially free from heavy metals comprising a water soluble, polymeric, quaternary ammonium compound having the formula:

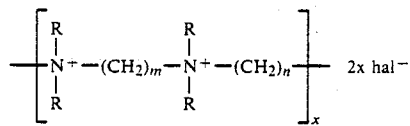

wherein R is a $C_1-C_7$ hydrocarbon group, m and n are a number from about 4 to 12 independently of the other, x is a number from about 10 to 300, and hal is chlorine, bromine or iodine.

2. The composition according to claim 1 further comprising an oxidizing agent.

3. The composition according to claim 2, wherein the oxidizing agent is selected from the group consisting of $K_2SO_5$ and $K_2S_2O_8$.

4. The composition according to claim 1, 2 or 3, wherein the composition is in the form of tablets.

5. The composition according to claim 1 wherein the composition is added to water to achieve a final concentration of more than 0.1 ppm.

* * * * *